United States Patent
Hsia et al.

(10) Patent No.: US 6,576,233 B2
(45) Date of Patent: Jun. 10, 2003

(54) DIETARY SUPPLEMENTATION WITH, AND METHODS FOR PREPARATION OF YEAST-DERIVED SELENIUM SALTS

(75) Inventors: Houn Simon Hsia, Irvine, CA (US); Ping Yang, Huntington Beach, CA (US); Michael Arnold, Irvine, CA (US)

(73) Assignee: Viva America Marketing, Inc., Costa Mesa, CA (US)

( * ) Notice: Subject to any disclaimer, the term of this patent is extended or adjusted under 35 U.S.C. 154(b) by 0 days.

(21) Appl. No.: 09/801,124

(22) Filed: Mar. 5, 2001

(65) Prior Publication Data

US 2001/0043925 A1 Nov. 22, 2001

Related U.S. Application Data

(60) Division of application No. 09/303,993, filed on May 3, 1999, now Pat. No. 6,197,295, which is a continuation-in-part of application No. 08/802,773, filed on Feb. 21, 1997, now abandoned, which is a continuation-in-part of application No. 08/719,572, filed on Sep. 25, 1996, now Pat. No. 6,140,107.

(51) Int. Cl.[7] .......................... A01N 63/04; C12N 1/18; C12N 1/16
(52) U.S. Cl. ................ 424/93.51; 435/255.1; 435/255.2; 435/940; 435/942
(58) Field of Search .................. 424/93.51; 435/255.1, 435/255.2, 940, 942

(56) References Cited

U.S. PATENT DOCUMENTS

| | | |
|---|---|---|
| 4,530,846 A | 7/1985 | Nagodawithana et al. |
| 4,617,189 A | 10/1986 | Stockel et al. |
| 4,784,852 A | 11/1988 | Johansson et al. |
| 6,197,295 B1 | 3/2001 | Hsia et al. |

OTHER PUBLICATIONS

Barnett et al., "Yeasts characteristics and identification," Cambridge University Pres. Second Edition, 1990, pp. 595–597.

Pei et al., "Anti–Cancer Drugs," 1997, vol. 8, pp. 231–237.

Schrauzer, G.N. et al. Observations on Human Selenium Supplementation. Trace Substances in Environmental Health, (1979) 13, pp. 64–67.

Schrauzer, G.N. and White, D.A., Selenium in Human Nutrition: Dietary Intakes and Effects of Supplementation Bioinorganic Chemistry, 8, pp. 303–318 (1978).

Kumpulainen, Jorma DSc, Salmenperä, Leena MD, Siimes, Martti A. MD, Koivistoinen, Pekka DSc Perheentupa, Jaakko MD, Selenium status of exclusively breast–fed infants as influenced by maternal organic or inorganic selenium supplementation[1-3], Amer. Jour. of Clinical Nutrition, vol. 42., No. 5, pp. 829–835.

Talaro, K. et al., "Physical and Chemical Control of Microbes" and "Environmental and Applied Microbiology" in Talaro, K. et al., Foundations in Microbiology (Wm. C. Brown Publishers, 1993), pp. 281–282, 741–742.

*Primary Examiner*—Sandra E. Saucier
*Assistant Examiner*—Vera Afremova
(74) *Attorney, Agent, or Firm*—Orrick, Herrington & Sutcliffe LLP; Kurt T. Mulville

(57) ABSTRACT

The present invention solves the need for non-toxic forms of selenium which is an essential part of the human diet. This invention provides novel dried-yeast products containing selenium as well as a method of producing the dried yeast products. The method uses selenium having high biological activity but low toxicity. The invention also provides nutritional supplements containing the novel selenium containing dried yeast products and methods of administering these products and supplements to improve human health. The invention also provides a practically non-toxic yeast selenium product having increased intracellular selenium concentrations and methods to reduce tumor cell growth by administration of a selenium yeast product in combination with chemotherapeutic agents. In particular, selenium yeast product of strain ATCC 74366.

5 Claims, No Drawings

DIETARY SUPPLEMENTATION WITH, AND METHODS FOR PREPARATION OF YEAST-DERIVED SELENIUM SALTS

CROSS-REFERENCE TO RELATED APPLICATION

This application is a divisional of U.S. patent application Ser. No. 09/303,993 filed May 3, 1999 and will issue as U.S. Pat. No. 6,197,295 on Mar. 6, 2001, which is a continuation-in-part of U.S. patent application Ser. No. 08/719,572, filed Sep. 25, 1996, which issued as U.S. Pat. No. 6,140,107 on Oct. 31, 2000, which is a continuation-in-part of U.S. patent application Ser. No. 08/802,773 filed Feb. 21, 1997 now abandoned and herein fully incorporated by reference.

BACKGROUND OF THE INVENTION

1. Field of the Invention

This invention relates to the field of human dietary supplements and more specifically to improved therapeutic products prepared from yeast and containing increased selenium concentrations with reduced toxicities.

2. Background

Selenium is an essential trace element for proper physiological function in humans. Decades ago, scientists demonstrated that selenium was incorporated into the chemical structure of an enzyme called glutathione peroxidase, an enzyme that is necessary to protect erythrocyte (red blood cell) cell membranes, and other biological structures against toxic reactions with highly reactive oxygen-derived species such as peroxides, and superoxides. The role of selenium in the biochemistry of glutathione peroxidase has been studied in some detail and the most current medical information confirms that trace amounts of selenium are required to maintain normal human health. Failure to ingest and absorb the necessary amounts of selenium can lead to improper functioning of the body's metabolic processes, and to various diseases and disorders.

Although many traditional nutrients, such as the natural occurring vitamins and minerals for which the U.S. Food and Drug Administration (FDA) has established a Recommended Daily Allowance (RDA), may be consumed in large quantities without adverse health effects, ingestion of high levels of some essential nutrients, such as certain metallic nutrients like selenium, may be toxic. To maintain ordinary health, one must balance the need for a minimum amount of such compounds with the need to protect against over-ingestion to the point of toxicity. For these compounds, ingesting low doses confers a significant nutritional benefit. However, when higher levels, i.e., amounts beyond the concentrations recognized as required for ordinary nutritional benefits, are ingested, beneficial health effects are not realized and the potential for dangerous toxicity exists.

Nutritionally beneficial quantities for daily doses for selenium have been found to be small. Nutritional selenium levels have been established by the FDA (see 21 C.F.R. 101.9(c)(8)(iv), January 1994). Humans and animals can safely metabolize limited amounts of both inorganic and organic forms of selenium and can convert non-methylated selenium to mono-ordi-or trimethylated derivatives, of which the monomethylated derivatives are most toxic. [Bedwal, R. S., et al., *Medical Hypotheses,* 41 (2):150–159 (August 1993)]. The FDA has adopted Reference Daily Intakes (RDIs) of 70 micrograms for selenium. Selenium dosage of 600 micrograms per day has been reported as safe. [Ferris G. M. Lloyd, et al., *App. Clin. Biochem.,*26:83–88 (1989)]. At about this dosage, normal activity of the enzyme glutathione reductase safely converts selenogluthatione to hydrogen selenide in the liver and erythrocytes and is ultimately excreted. Thus, at such lower dosages, the body is able to safely metabolize and excrete selenium that is present in the free metallic form.

For many years, physicians and medical researchers have studied several potential health benefits resulting from the ingestion of low levels of selenium. For example, low concentrations of sodium selenate (an inorganic form of selenium) work with vanadium to improve glucose tolerance and to increase the levels of glucose-induced insulin release. However, as with many trace elements such as selenium, at higher dosage levels or concentrations, these beneficial effects are reversed and dangerous toxicity is manifested. [Furnsinn, C. et al., *Internat'l J. of Obesity and Related Metab. Dis.,* 19(7):458–463 (1995)].

Therefore, the administration of selenium in the natural form involves a scientific and medical trade-off because, when administered in relatively low concentrations, selenium provides beneficial health effects, however, at higher concentrations, selenium exhibits dramatic toxicity such that the potential health benefits are lost and toxicity becomes the primary concern. This trade-off is particularly problematic when selenium administration is attempted, not as a dietary supplement, but rather in the treatment of disease. However, if the toxicity problems could be overcome, increased dosages of selenium could offer substantial advances in the treatment of several important disorders that affect human health. For example, the role of selenium in maintaining the function of the enzyme glutathione peroxidase has led researchers to examine the role of selenium in several disease states. In cancer, animal studies have shown that selenium protected against chemicals and ultraviolet energy sources known to cause cancer in humans. Selenium is believed to reduce the risk of certain cancers due to its properties as a strong antioxidant. A clinical study of more than 1,300 people found that those who took a daily supplement of selenium cut their overall cancer risk by nearly 40%. [Terence Monmaney, *Selenium May Fight Cancer, Study Shows,* LOS ANGELES TIMES, Dec. 25, 1996, at A 1, A 29]. In addition, U.S. Pat. No. 4,599,234 teaches that a combination of a selenium species (either organic or inorganic forms) with beta-carotene and a hydroxytoluene source significantly reduced the mortality of mice that were fed carcinogens and that these effects were better than those observed for the mice that were administered either selenium or beta-carotene or hydroxytoluene. U.S. Pat. No. 4,564,634 teaches a selenium-based nutritive composition having anti-neoplastic activity in which the selenium compound is used is a novel form of selenium prepared by a reaction of selenium metal with Tung oil (9,11,13-octadecatrienoic acid). [Schrauzer, G., *Inorg. and Nutr. Aspects of Cancer,* p. 330 (New York: Plenum Press (1978))].

Heart disease has also been shown to be reduced in persons who consume recommended amounts of selenium in their diet. In certain studies, the levels of selenium in the blood stream have been directly correlated with the degree of progression of cardiovascular disease with those patients having the lowest levels of selenium having the most extensive coronary artery blockage. In such cases, the glutathione peroxidase enzyme is thought to exert an antioxidant effect that protects the coronary vessels from disease. In a similar mechanism, selenium is thought to interact with prostaglandins to control free radical cascades that lead to elevated levels of prostaglandins and inflammation. Patients suffering from arthritis have been shown to have low levels of plasma selenium and their clinical condition has improved with dietary supplementation of selenium.

The precise mechanism by which selenium may protect from cardiovascular disease is not known, however, free radical antioxidant "scavengers," such as selenium, are believed to react with oxidants such that the oxidants are not available to form oxidized low density lipoproteins (O-LDLs). Thus, a reduction in the oxidants lowers the risk of arterial plaque deposits in blood vessels. Arterial plaque is precipitous material formed chiefly of oxidized low density lipoproteins (O-LDLs). The buildup of plaque in the form of O-LDL in the arteries is understood to be a factor in ischaemic heart disease. Free radical oxidants, many of which come from naturally occurring sources such as sun exposure, metabolism of certain nutrients, and exercise, act to oxidize low density lipoprotein (LDL) into its deleterious form, O-LDL. In contrast, high density lipoprotein (HDL) is understood to have beneficial health effects in the body. HDL is understood to be a more soluble form of lipoprotein, and its presence is not known to significantly contribute to the formation of arterial plaque. Since selenium functions to reduce the levels of O-LDL and thereby increase the level of HDL in the body, adequate quantities of selenium may decrease the likelihood of cardiovascular disease as well.

Based on the foregoing, increased concentrations of selenium are potential treatments for a variety of disorders as long as the selenium concentrations do not reach toxic levels. For this reason, several different forms of selenium have been investigated to determine the optimal form for administration to humans, either as a dietary supplement or as a therapeutic product for the treatment of disease. Yeast-derived selenium has been shown to be a less toxic form of selenium, and thus a preferred source of a selenium composition for human consumption. The selenium produced by yeast cultures undergoes a type of biosynthesis whereby inorganic selenium salts are converted to an organic form via intracellular incorporation into the yeast. These organic, biosynthesized selenium yeast derivatives are better nutritive sources of selenium because they are less toxic and more easily metabolized by the mammalian system than their inorganic counterparts. One method of producing a selenium-enriched product using food yeast such as *Saccharomyces cerevisiae* or *Candida utilis* has been reported. When dried and fed to rats, these selenium-enriched yeast effectively prevent hepatic liver necrosis. [Reed et al., *Yeast Tech.*, AVI Publ. Co., Conn. (1973)]. Unfortunately, this method results in the production of a yeast product having a low intracellular selenium content, as well as a relatively high extracellular concentration of inorganic selenium.

Generally, high extracellular concentrations of selenium are to be avoided, while higher intracellular concentrations are preferred because this tends to indicate an increased relative concentration of selenium in the organic form which, as noted above, is preferred for administration to humans. For this reason, prior efforts at producing selenium-based yeast products have focused on the ability to provide increased intracellular concentrations of selenium. For example, U.S. Pat. No. 4,530,846 ('846) describes a method for producing a selenium-enriched yeast that yields yeast with a moderately high intracellular selenium content. The yeast produced by this method are cultivated using a procedure that involves incremental feeding of the yeast culture. With respect to the process of the '846 Patent and the limitations on selenium concentration using that method, the '846 patent states: "While intracellular selenium contents of yeasts are preferably in a range of 1,000 ppm or more, even as high as 2,500 ppm, the process has, as its practical limitations, the capacity of the yeast to assimilate the selenium during the yeast growth cycle without adverse effects on yield due to the selenium additive to the nutrients." In addition to the recognized limitations on the ability to achieve higher concentrations of intracellular selenium, the prior art also demonstrates that the existing yeast-derived selenium products still exhibit substantial toxicity. For example, the $LD_{50}$ for the yeast product described in the '846 patent is reported by the assignee to be on the order of 7 mg per kilogram. In practice, the $LD_{50}$ rating for a product limits the amount that may be administered to a human as part of a nutritional program or as part of an overall therapy to treat a disease. A relatively high $LD_{50}$ is particularly disadvantageous when physicians or researchers attempt to administer an elevated selenium dosage, i.e., several times that recommended for dietary supplementation, in the treatment of disease.

There remains a need in the art for a yeast selenium product that provides high concentrations of selenium, preferably the organic form fixed in an intracellular form, that exhibits the lowest possible toxicities when measured by $LD_{50}$. Ideally, such a product would be provided by a method to produce selenium-enriched yeast that results in: (1) a high growth rate of selenium-enriched yeast; (2) selenium-enriched yeast with high intracellular selenium content; and (3) low toxicity.

SUMMARY OF THE INVENTION

The present invention overcomes the shortcomings of the prior art by providing a method for producing a composition of highly active nutritional selenium, where (1) the selenium source of the compositions of the present invention is the natural form of biosynthesized selenium; (2) the biosynthesized selenium is entirely metabolizable by the human system, and is substantially free of toxic substances; and (3) the process can be carried out efficiently and meets requirements important for commercial production.

Therefore, an object of the present invention is to provide a method for preparing biosynthesized selenium-yeast with high selenium activity and low toxicity.

It is a further object of the present invention to provide a method for the production of biosynthesized selenium having high nutritional value and low toxicity.

Another object of the present invention is to provide an improved synthetic form of nutritional selenium that is substantially similar to the naturally occurring selenium complexes found in selenium rich foods.

It is another object of the present invention to-provide a method for the production of selenium-enriched yeast, where the source of the yeast for metabolizing selenium substrate is a yeast strain such as *Saccharomyces cerevisae* or *Saccharomyces boulardii* sequela PY31.

It is a further object of the present invention to provide a form of selenium species that is essentially non-toxic to the human body.

It is another object of the present invention to-provide for methods for the treatment of disease by administering yeast-derived selenium in quantities greater than administered for dietary supplementation.

It is a further object of the present invention to provide nutritional supplements that incorporate the selenium-enriched yeast produced by these methods.

Another object of the present invention is to provide an increased dosage of selenium that is less toxic to the human body at higher dosages such that higher dosages can be administered, if desired, including the administration of yeast selenium with chemotherapeutic agents.

DETAILED DESCRIPTION OF THE INVENTION

The present invention relates to methods of cultivating yeast using selenium compounds resulting in a dried selenium-enriched yeast product with high biological activity, nutritional supplements comprising this dried yeast product, therapeutic products comprising this dried yeast product, uses of such dried yeast product to supplement the human diet, and methods to treat disease comprising administering dosages of selenium in combination with chemotherapeutic agents to reduce the growth of tumor cells.

The process for preparing the selenium-enriched yeast product that has a high intracellular content of organically bound trivalent selenium in a highly biologically active and non-toxic form comprises the steps of:

(1) preparing an aqueous mixture of yeast growth nutrients (aqueous media);

(2) preparing an aqueous solution of selenium salt in distilled water by dissolving the selenium salt in warm distilled water and then filtering the resulting selenium solution;

(3) adding the selenium solution to the yeast growth nutrients and mixing to form a selenium growth mixture;

(4) adding the selenium growth mixture, preferably by incremental addition, to a live yeast culture to form a selenium yeast growth solution and incubating with gentle shaking action or stirring;

(5) recovering and concentrating the yeast cells from the selenium yeast growth solution;

(6) washing the recovered yeast cells to remove extracellular selenium; and (7) pasteurizing and/or drying the washed yeast cells.

Growth media that can be used in the first—preparing step of present invention include 25° Brix molasses [TCT, Gold Coast], 38° Brix molasses [TCT, Gold Coast], glucose media, and potato dextrose broth. In addition, Brix molasses with a higher sugar content, e.g., 79° Brix [TCT, Gold Coast], may be used and then diluted with distilled water to form a Brix solution of lower sugar content. Numerous other growth media that are known to support the growth of yeast from the Saccharomyces family may be used and could be readily selected by one of skill in the art. In a preferred form, a mixture of different growth media may be used.

In addition, numerous vitamins and minerals may optionally be added to the yeast growth media. Such-vitamins and minerals are selected from those known in the art to help sustain proper yeast growth, including but not limited to biotin, vitamin $B_1$, vitamin $B_6$, calcium pantothenoate, inositol, copper, copper sulfate, zinc, zinc sulfate, iron, and iron sulfate.

The second preparing step in the process for producing the selenium-enriched yeast of the present invention involves preparing a selenium solution by dissolving selenium salt in distilled water and filtering the resultant selenium solution. The selenium may be in the form of an amorphous solid or an organoselenium compound. In a preferred form, sodium selenite may be used. In a preferred form, a cellulose acetate filter [Corning Scientific Co.] may be used. The resultant filtered selenium solution has between about 100 ppm and 40,000 ppm selenium.

The first addition step involves adding the selenium solution to the yeast growth nutrients (aqueous media) to form a selenium growth mixture. Once the selenium solution is added, the selenium and media may be mixed by gentle shaking action or stirring for between about 1 and about 30 minutes.

In the second addition step, the selenium growth mixture is added to live yeast cells to make a selenium yeast growth solution having selenium levels between about 100 ppm and about 20,000 ppm selenium, preferably between about 200 ppm to about 10,000 ppm, and most preferably between about 250 ppm to about 1,500 ppm of selenium. The second addition step preferably involves adding the selenium growth mixture to the yeast culture incrementally. This second addition step preferably takes place under a controlled pH of from about 4.2 to about 6.0, and preferably from about 4.5 to 5.3. This second addition step also preferably takes place at a temperature from about 20° C. to About 35° C., and preferably about 28° C. to about 32° C.

The yeast employed in the second addition step preferably a food grade or edible yeast, and most preferably *Saccharomyces boulardii* sequela PY31. Other yeast which can be used include *Saccharomyces cerevisae* or *Saccharomyces torula*.

As stated above, the present invention may also employ a newly isolated and purified strain of yeast, *Saccharomyces boulardii* sequela PY31. Specifically, *Saccharomyces cerevisiae* and *Saccharomyces boulardii* sequela are of the same genus, and *Saccharomyces boulardii* sequela is described as a synonym of *Saccharomyces cerevisiae*. More particularly, the novel yeast strain *Saccharomyces boulardii* sequela PY31 may be isolated from raw soil samples, and cultivated to yield quantities of yeast at a scale sufficient for developmental research and for production of commercial products. The novel strain of yeast, *Saccharomyces boulardii* sequela PY31, has been deposited in an International Repository in accord with the Budapest Treaty and has been assigned ATCC No. 74,366. ATCC American Type Culture Collection, 10801 University Boulevard, Manassas, Va. 20110-2209. This novel yeast strain is described in co-pending application Ser. No. 08/719,572 filed on Sep. 25, 1996. This strain may be analyzed according to the principle of cellular fatty acid analysis, to obtain a quantitative measurement of relatedness to *Saccharomyces cerevisae* based on their fatty acid make-up. A Euclidian Distance of less than 2.5 indicates that two yeast samples are most likely the same strain. A Euclidian Distance of less than 6.0 indicates the isolates are most likely the same subspecies and a Euclidian Distance of less than 10.0 indicates the isolates are most likely the same species. The greater the distance between the isolates, the closer the relationship taxonomically. In the present invention, the Euclidian Distance between the submitted strain (*Saccharomyces boulardii* PY-3-1) and LIBR *S. cerevisae* is 7.48, which indicates that these isolates are most likely the same subspecies, but the submitted strain is not very close to LIBR *S. cerevisae* due to the remote Euclidian Distance.

Specifically, the method for isolating this novel yeast strain, *Saccharomyces boulardii* sequela PY31, comprises:

(1) identifying a location for collection of a soil sample, which is proximal to a germanium mine (i.e., within 100 yards of a germanium mine);

(2) sampling the soil by removing about 200 g from a depth of 5 cm to 20 cm, and transporting the sample using a sterilized bag;

(3) growing the living material on three different mediums which support the growth of all yeast, and that selectively kills bacteria without killing the yeast;

(4) separating the yeast from other living matter and then repeating this process until yeast can be grown without bacterial contaminants;

(5) selecting and restreaking the yeast colonies, and repeating this process three times;

(6) selecting the yeast colonies most vital for growth in a medium enriched with germanium;

(7) growing each selected colony on malt extract agar or dextrose agar, and selecting which colonies appear most robust, and;

(8) cultivating the selected yeast by growing 1–2 slants of the yeast for about 2 days at about 30° C. and then transferring to the cultivated yeast about 100 mL of malt extract broth and then incubating at about 30° C. for 8–10 hours, then adding to the incubated mixture about 500 mL of malt extract broth and then growing the resulting mixture at about 30° C. for about 6 to about 14 hours.

The present invention also teaches a use of this novel yeast strain, *Saccharomyces boulardii* sequela PY31, to prepare selenium-enriched, non-toxic yeast forms according to the method described herein.

As part of the second addition step, the selenium yeast growth solution is incubated to induce yeast growth. The incubation may occur with shaking or stirring at about 200 rpm for a period of about 5 hours to about 75 hours, preferably from about 15 hours to about 60 hours, and most preferably about 20 hours. This incubation occurs at a temperature of about 25° C. to about 30° C., and preferably about 30° C.

The yeast cells are then isolated from the selenium yeast growth solution by centrifuging the selenium yeast growth solution, and isolating the yeast cells. In a preferred form, the centrifugation step may occur at about 3,900 rpm.

The isolated yeast cells are then washed to remove extracellular selenium. The washing step may involve washing the isolated yeast cells between 2 and 20 times with aqueous solvent, such as a buffered aqueous solution that optionally contains chelating agents such as EDTA.

Lastly, the yeast cells are pasteurized and/or dried to produce a dried yeast product. The pasteurization step may occur at between about 30° C. and about 110° C., preferably at about 60° C. The resulting dried yeast product may contain from about 300 ppm to about 6,000 ppm intracellular selenium, but preferably contains more than 1000 ppm intracellular selenium, and most preferably between about 2000 ppm and about 5000 ppm.

The present invention also relates to the use of the dried selenium-enriched yeast products as dietary supplements. To prepare the yeast compositions of the invention for use as a dietary supplement, the dried yeast product is combined as the active ingredient in intimate admixture with a suitable carrier according to conventional compounding techniques. This carrier may take a wide variety of forms depending upon the form of preparation desired for administration, e.g., oral, sublingual, nasal, or parenteral.

In preparing the compositions in oral dosage form, any of the usual pharmaceutical media may be employed. For oral liquid preparations (e.g., suspensions, elixirs, and solutions), media containing for example, water, oils, alcohols, flavoring agents, preservatives, coloring agents and the like may be used. Carriers such as starches, sugars, diluents, granulating agents, lubricants, binders, disintegrating agents, and the like may be used to prepare oral solids (e.g., powders, capsules, pills, and tablets). Controlled release forms may also be used. Because of their ease in administration, tablets, pills, and capsules represent advantageous oral dosage unit forms, in which cases solid pharmaceutical carriers are obviously employed. If desired, tablets may be sugar coated or enteric coated by standard techniques.

For parenteral products the carrier will usually comprise sterile water, although other ingredients may be included, e.g., to aid solubility or for preservation purposes. Injectable suspensions may also be prepared, in which case appropriate liquid carriers, suspending agents, adjuvants, and the like may be employed.

For dietary supplementation, a composition of the present invention is generally effective when parenterally administered in amounts ranging from about 1 mg of dried yeast per dose (1 dose per body weight of about 75 kg) to about 200 mg/dose of composition. A preferred amount is from about 10 mg/dose to about 50 mg/dose, and most preferred at about 20 mg/dose. This dosage of the composition translates to an amount of from about 1 $\mu$g/dose to about 200 $\mu$g/dose of selenium, preferably from about 10 $\mu$g/dose to about 50 $\mu$g/dose of selenium, and most preferably about 20 $\mu$g/dose of selenium. When orally administered, the compositions of the present invention are generally effective in approximately the same amounts as the parenteral products. Activity at this level makes the compositions particularly well suited for formulations in tablet size for oral administration. The above dosage ranges are likely to be administered at varying periods for humans, for example, from daily administration to administration at least 5 times per week. However, ultimately, the dosage regimen will depend upon the particular needs of the user. A preferred dosage regimen for dietary supplementation in humans is 1–2 doses per day.

The following examples are illustrative only and do not limit the invention in any fashion. Examples 1–3 demonstrate a process to yield a selenium yeast product having in intracellular yeast concentration of greater than 1000, greater than 1800 and approximately 2000 ppm.

EXAMPLE 1

The growth medium was prepared as follows. 79° Brix molasses (1000 g) from TCT, Gold Coast was diluted to 1 L with distilled water resulting in a 32° Brix solution. Then, 4.12 g of KCl was added, followed by 4.12 g of MgSO$_4$.7H2O and then 44.4 g of NH$_4$HPO$_4$, and the resulting mixture was stirred to homogeneity. To this mixture was added enough water to reach a final volume of 2 L, and thus a 32° Brix molasses. The mixture was tested for sugar content by using a Brix refractometer [Cole-Palmer Instrument Co., RH13-32ATC], and the final pH was adjusted to 5.0 with HCl or NaOH. This solution was then autoclaved at 105° C. for 15 minutes. A stock solution of sodium selenate was prepared as follows. To 300 mL of distilled water at ambient temperature was added 9.0 g of sodium selenate and the resulting mixture was kept at ambient temperature for 1 hour, then filtered through cellulose acetate membrane [Coming Scientific Co].

The selenium growth mixture was prepared by adding 60 mL of the stock selenium solution to 1300 mL of 32° Brix molasses mixture (pH 5.07) and 3140 mL of water.

The yeast culture was prepared as follows. One slant of yeast were incubated for two days at 30° C., and then grown at 30° C. in 200 mL of Malt extract, shaken at 200 rpm for 8 hrs, and then to this was added 300 mL of malt extract and the resulting mixture was incubated at 30° C. overnight with shaking.

The yeast were cultivated as follows. 500 mL of a solution of *Saccharomyces boulardii* sequela PY31 was dissolved in 500 mL of distilled water and stirred at 500 rpm in a 7 L fermentation apparatus [Bioflow 2000, New Brunswick]. To this yeast culture, 4500 mL of the selenium growth mixture as added under an air flow of about 2 to about 5 L/min and over a period of about 6 hours at about 30° C. The resulting suspension was stirred for an additional 15 hours.

The resulting selenium yeast growth solution was then centrifuged at 3900 rpm for 10 minutes, and resulting-yeast cream (isolated yeast cells) was washed five times with a total volume of 8 L of water.

The resulting yeast cells were dried at less than 80° C. until a moisture content of 2–3% was obtained. The selenium was kept at ambient temperature for 1 hour, then filtered through cellulose acetate membrane [Coming Scientific Co].

The selenium growth mixture was prepared by adding 60 mL of the stock selenium solution to 1300 mL of 32° Brix molasses 5 mixture (pH 5.07) and 3140 mL of water.

The yeast culture was prepared as follows. One slant of yeast were incubated for two days at 30° C., and then grown at 30° C. in 200 mL of Malt extract, shaken at 200 rpm for 8 hrs, and then to this was added 300 mL of malt extract and the resulting mixture was incubated at 30° C. overnight with shaking.

The yeast were cultivated as follows. 500 mL of a solution of *Saccharomyces boulardii* sequela PY31 was dissolved in 500 niL of distilled water and stirred at 500 rpm in a 7 L fermentation apparatus [Bioflow 2000, New Brunswick]. To this yeast cultures 4500 mL of the selenium growth mixture as added under an air flow of about 2 to about 5 L/min and over a period of about 6 hours at about 30° C. The resulting suspension was stirred for an additional 15 hours.

The resulting selenium yeast growth solution was then centrifuged at 3900 rpm for 10 minutes, and resulting yeast cream (isolated yeast cells) was washed five times with a total volume of 8 L of water.

The resulting yeast cells were dried at less than 80° C. until a moisture content of 2–3% was obtained. The selenium content of the yeast was measured using atomic absorption techniques to give a yeast mass having 1839 ppm of selenium. As noted above and in the following examples, the concentration of intracellular selenium can be modified by adjusting the concentration of selenium in the stock solution of sodium selenate also, the process steps can be manipulated as described herein to alter the final selenium concentrations in the yeast product. The final intracellular selenium concentration is preferably greater than 1000 ppm, preferably greater than about 2000 ppm, and as high as about 5000 ppm and exhibits non-toxicity as measured by $LD_{50}$ such that doses of the yeast product of the invention equivalent to greater than 7 mg/kg in rats, can be administered without toxicity, including amounts as high as 5.0 g/kg or higher. The resulting selenium yeast product of the invention meets the requirements of the Limit Test as set forth in the "Toxicological Principle for the Safety Assessment of Direct Food Additives and Colour Additives Used in Food."

EXAMPLE 2

The method described in Example 1 was repeated to give a dried yeast mass having a final concentration of selenium of 1849 ppm.

EXAMPLE 3

Examples 3 and 4 describe a process to produce a yeast product having increased selenium concentrations, specifically greater than 4500 ppm and approximately 5000 ppm.

The yeast growth nutrients were prepared as follows. 25° Brix molasses (670 g) [TCT, Gold Coast] was diluted to 1 L with distilled water, then 2.72 g of KCl was added, followed by 2.72 g of $M9SO_4 \cdot 7H2O$ and then 29.28 g of $NH_4HPO_4$, and then enough water was added to reach a final volume of 2 L, and the resulting mixture stirred at ambient temperature until homogenous. The mixture was tested for sugar content by using a Brix refractometer [Cole-Palmer Instrument Co., RH13-32ATC], and the final pH was adjusted to 5.0. This solution was autoclaved at 105° C. for 15 minutes.

A stock solution (3%) of sodium selenate was prepared as follows. To 300 ML of distilled water at ambient temperature was added 9.0 g of sodium selenate and the resulting mixture was stirred at ambient temperature for 1 hour. The resulting selenium solution was filtered through cellulose acetate membrane [Coming Scientific Co].

The yeast culture was prepared as follows. One slant of yeast were incubated for two days at 30° C., and then grown at 30° C. in 200 mL of Malt extract, shaken at 200 rpm for 8 hrs, and then to this was added 300 mL of malt extract and the resulting mixture was incubated at 30° C. overnight with shaking.

A yeast growth mixture was prepared by adding 13.2 L of the selenium solution (3%) to 3989 mL of the 25° Brix molasses and 247 mL of water, and then stirred or shaken to homogeneity.

The cultivation of selenium-enriched yeast was undertaken as follows. In a 7 L fermentation apparatus [Bioflow 2000, New Brunswick] containing 70 mL of a stirred (500 rpm) yeast culture of *Saccharomyces boulardii* sequela PY31, 2 L of the yeast growth nutrient mixture was added over 8 hours at 30° C. with stirring under an air flow of about 2 to about 5 L/min. After the addition of the yeast growth nutrient mixture, the mixture was stirred an additional 5 hours at about 500 rpm. Then, 3989 mL of 25° Brix molasses growth nutrients and 247 mL of water were added, and the resulting selenium yeast growth solution was shaken at 200 ppm for 24 hours at 30° C.

The resulting selenium yeast growth solution was centrifuged at 3,900 rpm for 10 minutes, the supernatant removed, then the yeast cells were washed once with 100 mL of EDTA (pH=7.8), once with 100 mL of 0.01 M $Na_2HPO_4$ buffer solution, and five times with 100 mL of distilled water.

The resulting yeast cream (isolated yeast cells) was dried in vacuo and then the selenium content of the yeast was measured using atomic absorption techniques to give a yeast mass having 4857 ppm of selenium.

EXAMPLE 4

The method of Example 3 was repeated and yielded a final dried yeast mass having a concentration of selenium of 4945 ppm.

EXAMPLE 5

A 20% glucose media was prepared by adding 400 g of glucose, with stirring, to 2 L of distilled water, followed by addition of 43 g of urea, 20 g of $Na_2HPO_{4,}$ 7.6 g of $MgSO_4 \cdot 7H_2O$, 4.4 g of KCl, 50 g of sodium citrate, and 10 grams of yeast extract [DIFCO, Bacto]. The resulting yeast growth nutrients were mixed and then autoclaved at 10 psi for 15 minutes.

A vitamin mixture was prepared as follows: 4 mg solid biotin, 8 mg vitamin B1, 200 mg vitamin B6, 100 mg calcium pantothenoate, and 2 g of inositol were added to 100 mL of distilled water, and the resultant solution was stirred to homogeneity and filtered through a 25 micron cellulose acetate filter [Watman].

A mineral solution was prepared as follows: 0.5 g of $CuSO_4.5H_2O$, 8 g of $ZnSO_4.7H_2O$, and 3 g ferric sulfate $(Fe(SO_4)_2(NH_4)_2.6H_2O)$ were added to 1 L of distilled water and stirred to homogeneity and then autoclaved at 10 psi for 15 minutes.

A yeast growth nutrient mixture was prepared by adding 20 mL of the vitamin solution and 2 mL of the mineral solution to the glucose media.

The yeast culture was prepared as follows. One slant of yeast were incubated for two days at 30° C., and then grown at 30° C. in 200 mL of Malt extract, shaken at 200 rpm for 8 hrs, and then to this was added 300 mL of malt extract and the resulting mixture was incubated at 30° C. overnight with shaking.

A cultivation of selenium-enriched yeast was undertaken by adding 50 mL of 3% sodium selenate solution (as described in the above examples) to 2,500 mL of the 20% yeast growth nutrient mixture. Next, 2 L of the resulting mixture was isolated and added slowly over a period of 11 hours at 31° C. to a mixture of 500 mL *Saccharomyces boulardii* sequela PY31 (ATCC No. 74,366) and 2 L distilled water that had been mixed to homogeneity and autoclaved at 10 psi for 15 minutes. The resulting selenium yeast growth solution was then stirred at 31° C. for an additional 8 hours.

The yeast were then isolated as described in Example 1 above to yield yeast mass containing 684 ppm selenium.

EXAMPLE 6

A determination of toxicity of the yeast product of the present invention was conducted in the Rat Acute Oral Toxicity Model for comparison with the reported values in existing selenium yeast products and specifically for those described in U.S. Pat. No. 4,530,846 ($LD_{50}$ indicates toxicity at 7 mg/kg). The Rat Acute Oral Toxicity Study was carried out on the yeast selenium product of the invention at 1.0, 2.0, 3.0 and 6.0 g/kg body weight. Groups consisted of 3 male rats per dose level. No mortalities or toxic symptoms were observed at any of these dose levels.

Based on the results of this toxicity testing, a limit test was performed using one dose level of 5.0 g/kg body weight. The test article was suspended in 1% methylcellulose (w/v.) 15.0 g of the test article was suspended in 60.0 mL: of 1% methylcellulose and thoroughly blended by use of a Polytron® homogenizer. The test article was administered through a feeding cannula at a dose level (by volume) of 20.0 mL/kg. The test group consisted of 5 male and 5 female rats. No mortalities or other toxic symptoms were observed during the 14-day study period, and all animals gained body weight by the end of the study. No gross pathological findings were observed at the end of the study.

Based on the above findings, the yeast selenium product of this invention is classified as "practically non-toxic" by oral ingestion and the $LD_{50}$ for the product was determined to be in excess of 5.0 g/kg.

EXAMPLE 7

As noted above, the administration of a selenium yeast product can be indicated in the treatment of disease. Because the selenium yeast product of this invention demonstrates low toxicity, the selenium yeast product can be readily administered with other therapeutic compounds including chemotherapeutic agents to reduce the growth of tumor cells. For example, the anti-neoplastic effect of the selenium yeast product of the invention have been investigated on the following tumor cells in vitro; Breast (MCF-7, MCF-10, SKBR-3), Lung ($RH_2$), Prostate (LNCap and PC-3), Colon (T84, Caco-2), Small Intestine (HCF8), and Liver (HepG2). In addition, we examined additive or synergistic effect of the selenium yeast product in combination with standard anticancer drugs, adriamycin and taxol. The effect of the administration of the selenium yeast product was assessed with the following measurements: apoptosis; DNA synthesis; growth rate by MTT assay; uptake of amino acid MeAIB by System A; and morphological changes by the tunnel assay. The selenium yeast caused increase in apoptosis as measured by DNA fragmentation and increase in "rounded" cells and membrane "blebbing," decrease in MeAIB uptake, and decrease in DNA synthesis in breast cancer cells MCF-7 and SKBR-3. These changes were selenium dose dependent with optimal inhibition at a selenium concentration between 4 and 40 ng/ml after 72 hrs of treatment. Similar observations were with lung (RH2), small intestine (HCF8), colon (Caco-2), and liver (HepG2) cells. In contrast, prostate cancer cells LNCap and PC-3, and the colon cancers cells T-84 were not significantly affected by administration of the selenium yeast product alone. However, addition of adriamycin or taxol in combination with selenium inhibited growth of prostate cancer cells. Addition of a chemotherapeutic agent, in this case, taxol or adriamycin, with the selenium product caused further inhibition of MCF-7, SKBR-3, RH2, HCF8, and HepG2 cells. Thus, the selenium yeast product had a significant in vitro anti-neoplastic effect on breast, lung, liver, and small intestinal tumor cells. Supplementation of the anti-neoplastic therapy with the selenium yeast product potentiated chemotherapeutic effects of taxol and adriamycin in the cancer cell lines indicated above. Thus, a preferred method of this invention is the administration of a selenium yeast product in combination with a chemotherapeutic agent such as Adriamycin, Doxil, Mitoxantrone, Mitomycin C, Actinomycin, Cytoxan, Bleomycin, BCNA (Carmustine), Velban, Vincristine, Epotoside, Prednisone, Xeloda, S-Fluorouracil, Camptosar, Carboplatin, Cis-Platin, Taxol, Taxatere, Herceptin, Methotrexate, Hycroxyurea, Cytosar, Gemcytabine, Nitrogen Mustard, Procarbazine, Imidazove Carboxamide (Dacarbaziin), Tamoxifen, Estracyte, Jupron, Flutamide, Daunarubicin, Lomostine, Ifusfamide, Mesna, Streptozocin, Interferon, Dexamethasone, Melphalan, Leulovorin, Chlorambucil, Fludarabine, Busulfan, Interleurine-2, Navelbine, Gmerocapto-Purina, and Megestroc.

EXAMPLE 8

As noted above, the yeast products of the invention exhibit significantly lower toxicities compared to other selenium yeast products manufactured with existing techniquest and with non-proprietary yeast strains such as ordinary *Saccharomyces cerevisae* (Brewer's Yeast).

To compare the advantage of the yeast strains described herein with ordinary *S. cerevisae*, about 1 g of each yeast strain sample (a total of 10 samples were collected) was added to 99 ml of malt broth (pH 4.7, DIFCO), shaken at 200 rpm at 30° C. for 2 days. The fungal conidia germinate and form small mycelia balls that do not form new conidia (Rose et al., 1987). After two days of growth, the culture solution was filtered though the sterilized glass wool and the fungal mycelium could be filtered off over the wool. Serial dilution (10 fold) of the filtrate were made and then streaked onto three types of agars with 0.1% chlorophenicol or ampicillin (50 ug/L), including malt extract agar (pH 4.7, DIFCO), sabouraud dextrose agar (pH 5.6, DIFCO), and potato dextrose agar (pH 5.6, DIFCO). The colonies were selected under microscope and restreaked after 2–7 days of incubation at 28° C. This procedure was repeated at least 3 times.

Yeast stocks were maintained at 30° C. on malt agar (DIFCO) or sabouraud dextrose agar (DIFCO). For most experiments, cultures were grown in a molasses medium had the following composition (g L-1): 79° Brix molasses JCT, Gold Coast, Calif.), 80.8; KCI, 0.33; MgSO4, 0.33; NH4H2PO4, 3.6; pH 4.5–5.0. pH was adjusted to 4.5–5.0 using HCI. The cultures were allowed to grow to A 590=(log phase, 1.2–2.4×10$^6$ cell/ml) prior to use. Cell numbers and percentage of budding cells and dead cells were determined using a haemocytometer after appropriate dilution with distilled water and staining with 0.4% trypan blue solution (sigma, St, Louis, Mo.). The size of yeast populations in aqueous suspensions was determined using optical density (OD590) measurements.

The yeast strains (YP3-1 *Saccharomyces boulardii* Sequela, ATCC 9763 and ATCC 96473), were allowed to grow to 1–2×10$^6$ cell/ml in the malt broth medium, followed by incrementally feeding with molasses (Gold Coast, Calif.) and sodium selenate (Sigma, St. Louis, Mo.). The final resulting mixture containing 300–400 ppm of sodium selenate and 5–6° Brix of molasses was incubated at shaker (260 rpm, 30° C.) or at the fermentor (BIOFLO 2000 FERMENTOR, New Brunswick Scientific, Edison, N.J.) at 600 rpm, 3 L/min and 30T. After 21–27 hr of incubation, this mixture was centrifuged at 3,900 rpm for 10 minutes, the supernatant removed, then the yeast cells were washed once with 0.1 M EDTA (pH=7.8) and 0.01 M Na$_2$HPO$_4$ buffer solution, and then five times with distilled water. The resulting yeast cream was dried in 80° C. oven for 2–3 days.

The selenium concentration in Se-yeast product was measured using an atomic absorption spectrometer (Perkin Elmer, Norwalk, Conn., Model 3 1 00). To accomplish this measurement, the dried yeast sample was digested in concentrated HNO$_3$ for four hours under a hood. Then, its selenium content was measured using an atomic absorption spectrometer set at a wavelength of 196.0 nm and a selenium lamp current at 16 mA.

The yeast strains were selected based on its superior vitality when grown in the presence of 1 ml aliquots of growing yeast culture containing 200, 300, 400, and 500 ppm of sodium selenate. After incubation at 30° C. for 1 day, the culture was streaked on malt extract agar, potato dextrose agar and sabouraud dextrose agar. The yeast (YP 3-1), gobose and budding cells, was growing well in solution containing sodium selenate under the concentration of 400 ppm and was selected from sabouraud dextrose agar with ampicillin. The colony characteristics of this yeast were described as dull creamy, non-mucoid, slight raised colonies on YM agar. ATCC 9763 and ATCC 96473) were commercially obtained from ATCC.

Table 1 and table 2 show the comparison of three strains in Se uptake ability and yeast growth characteristics by shaker and BF 2000 fermentor. Both experiments show less dead cells, higher mass and higher selenium concentrations in YP3-1 yeast product than that in control. In table 1, YP3-1 yeast produced 17.2% and 26.0% more dry mass containing 10.6% and 7.1% more cellular selenium than that from ATCC 9763 and ATCC 96473 yeast. More significantly in table 2, YP3-1 yeast produced 28.9% and 32.0% more dry mass containing 34.6% and 18.6% more cellular selenium than that from ATCC 9763 and ATCC 96473 yeast. The results indicate that selected yeast strain (YP31) has higher ability to assimilate selenium and shows efficient sugar utilization, higher toxic tolerance to selenium and better fermentation rate compared to the yeast strains tested.

TABLE 1

Se accumulation of different yeast strains in shaker

| Yeast strain | yeast quality (after fermentation) | dry weight (g) | Se concentration in final Se-yeast (ppm) |
|---|---|---|---|
| 3-1 | 1.34 × 10$^8$ cell/ml 33% budding 1.1% dead cell | 2.15 | 2406 |
| ATCC 9763 | 4.44 × 10$^7$ cell/ml 48.4% budding 12.7% dead cell | 1.78 | 2150 |
| ATCC 96473 | 2.82 × 10$^7$ cell/ml 41.3% budding 3.75% dead cell | 1.59 | 2235 |

To 50 ml of yeast culture (YP 3-1, ATCC 9763, and ATCC 96473) and 349 ml of dH2O, 6.5 ml of 3% Sodium selenate and 95 ml of 32° Brix molasses mix (pH 4.68) were incrementally fed. The mix (total 500 ml) containing 390 ppm Na2SeO4 compound, 6°B molasses mix and 10% yeast culture was incubated in a shaker at 260 rpm, 30° C. for 27 hrs. The yeast recovery and drying process were as described above and the results are an average of 3 experiments.

TABLE 2

Se accumulation of different yeast strains in fermentor

| Yeast strain | yeast quality (after fermentation) | wet weight (g) | solid weight (g) | Se concentration in final Se-yeast (ppm) |
|---|---|---|---|---|
| 3-1 | 3.41 × 10$^7$ cell/ml 22.67% budding 0.34% dead cell | 161 | 29.1 | 1418 |
| ATCC 9763 | 2.4 × 10$^7$ cell/ml 21.3% budding 2.3% dead cell | 119 | 20.7 | 928 |
| ATCC 96473 | 1.1 × 10$^7$ cell/ml 10.32% budding 0.45% dead cell | 114 | 19.80 | 1154 |

To 500 ml of pure yeast culture (YP 3-1, ATCC 9763, and ATCC 96473) and 3435 ml of dH$_2$O, 65 ml of 3% Sodium selenate, 150 ml of dH$_2$O and 853 ml of 32° Brix molasses mix (pH 4.68) were incrementally fed to BF 2000 fermentor. The mix (total 5 L) containing 390 ppm sodium selenate compound, 5.45°B molasses mix and 10% yeast culture was incubated in the fermentor at 600 rpm, 30° C. for 21–21.5 hrs. The yeast recovery and drying process were as described above and the results are from the average of three duplicate experiments.

Numerous modifications and variations of the present invention are included in the above-identified specification and are expected to be obvious to one of skill in the art. It is also intended that the present invention cover modifications and variations of the dried yeast selenium compositions and method for using them to accomplish their claimed uses within the scope of the appended claims and their equivalents.

We claim:

1. A composition comprising:
   a chemotherapeutic agent, and
   a composition for oral administration containing dried selenium yeast of the strain ATCC 74366 having an $LD_{50}$ greater than 7 mg/kg measured in a Rat Acute Oral Toxicity Model and an intracellular selenium concentration of between greater than 2000 ppm and 5000 ppm.

2. The composition of claim 1, wherein the chemotherapeutic agent is selected from the group consisting of Adriamycin, Doxil, Mitoxantrone, Mitomycin C, Actinomycin, Cytoxan, Bleomycin, BCNA (Carmustine), Velban, Vincristine, Epotoside, Prednisone, Xeloda, S-Fluorouracil, Camptosar, Carboplatin, Cis-Platin, Taxol, Taxatere, Herceptin, Methotrexate, Hydroxyurea, Cytosar, Gemcytabine, Nitrogen Mustard, Procarbazine, Imidazove Carboxamide (Dacarbaziin), Tamoxifen, Estracyte, Jupron, Flutamide, Daunarubicin, Lomostine, Ifusfamide, Mesna, Streptozocin, Interferon, Dexamethasone, Melphalan, Leulovorin, Chlorambucil, Fludarabine, Busulfan, Interleurine-2, Navelbine, Gmerocapto-Purina, and Megestroc.

3. The composition of claim 1, wherein the chemotherapeutic agent is taxol or adriamycin.

4. The composition of claim 1, wherein the dried selenium yeast is combined with a carrier for oral administration as a solid.

5. The composition of claim 4, wherein the carrier is selected from the group consisting of starches, sugars, diluents, granulating agents, lubricating agents, binders and disintegrating agents.

* * * * *